(12) United States Patent
Mikkanen et al.

(10) Patent No.: US 7,759,131 B2
(45) Date of Patent: Jul. 20, 2010

(54) DEVICE AND A METHOD FOR DILUTING A SAMPLE

(75) Inventors: Pirita Mikkanen, Tampere (FI); Tuomas Koskinen, Tampere (FI)

(73) Assignee: Dekati Oy, Tampere (FI)

( * ) Notice: Subject to any disclaimer, the term of this patent is extended or adjusted under 35 U.S.C. 154(b) by 1962 days.

(21) Appl. No.: 10/173,580

(22) Filed: Jun. 18, 2002

(65) Prior Publication Data

US 2003/0232449 A1 Dec. 18, 2003

(51) Int. Cl.
*G01N 1/38* (2006.01)
*G01N 1/00* (2006.01)

(52) U.S. Cl. .................... 436/179; 73/863.03

(58) Field of Classification Search ............ 436/47, 436/52, 179; 73/863.03
See application file for complete search history.

(56) References Cited

U.S. PATENT DOCUMENTS

| | | | | |
|---|---|---|---|---|
| 4,004,882 A | * | 1/1977 | Byrne et al. | 422/83 |
| 5,052,476 A | * | 10/1991 | Sukumoda et al. | 165/133 |
| 5,058,440 A | * | 10/1991 | Graze, Jr. | 73/863.83 |
| 6,211,956 B1 | * | 4/2001 | Nicoli | 356/337 |
| 2003/0213311 A1 | * | 11/2003 | Graze, Jr. | 73/864 |

* cited by examiner

*Primary Examiner*—Duane Smith
*Assistant Examiner*—Paul S Hyun
(74) *Attorney, Agent, or Firm*—Venable LLP; Eric J. Franklin

(57) ABSTRACT

A device and a method for diluting a sample are disclosed. A sample is first diluted by a porous tube type diluter configuration. Then the diluted flow is further diluted by a ejector type diluter configuration. Further a heat exchange based on serrature heat exchange elements inside said porous tube type diluter configuration is disclosed.

9 Claims, 3 Drawing Sheets

DEVICE AND A METHOD FOR DILUTING A SAMPLE

FIELD OF THE INVENTION

The present invention relates to sampling. More particularly the invention relates to a method and a device for taking a sample without causing unwanted changes to the medium to be studied, but at the same time taking necessary steps to pre-process the sample to a form more suitable for the analysis carried out.

BACKGROUND OF THE INVENTION

The process of sampling is an important part of any analysis or measurement where the actual analysis or measurement is made outside of the volume actually containing the process or medium to be studied.

In FIG. 1. a prior art solution for sampling is presented. The object is to study characteristics of a process inside volume 11. A probe 12 is inserted to the volume 11 through which a sample is transferred to a pre-processor means 13 outside the volume 11. In the pre-processor means 13 the extracted sample is processed so that it is better suited for the actual measurement carried out by the analyser 14. Some possible pre-processing processes comprise lowering the temperature of the sample and diluting.

Pre-processing is an important step of the sampling as it is the object to measure the process in volume 11 and as the pre-processing happens before the actual analysis all the modifications made in the pre-processing effects the result of the analysis. Thus a good pre-processing step is such that it will have a minimal effect on the characteristics to be analysed, but at the same time carrying out the modifications of the non-essential characteristics so that the sample can be analysed by the analyser.

Diluting is one of the most important methods of sample pre-processing for gaseous medium. In a dilution process air, or some another dilution medium, is mixed with a sample flow. The dilution ratio, i.e. ratio between dilution flow and sample flow, varies quite a lot depending e.g. of the analysis method to be used. For example in flue gas analysis dilution ratios 10-100 are commonly used. Dilution ratio is one of the major parameters to keep track of because it has direct effect on the measurement result as the measurement is made on the diluted sample.

Another important parameter of pre-processing is temperature. This is especially important when analyzing gaseous samples prone to chemical reactions or vapour condensation. These kind of measurements comprise e.g. exhaust gas measurement.

Thus a good sample pre-processing process for a hot gaseous medium would be such that it would allow good control over dilution ratio and temperature.

The prior art solutions include use of diluters based on porous tubes. One example is presented in FIG 2. The sample flow 21 is directed into a central cavity 29 of a porous tube. At the same time dilution air 22 is directed to the tube so that it will enter the central cavity 29 through the walls of the cavity. Sample flow 21 and dilution flow 22 will mix and produce a diluted flow 23 which is directed to an analyser 14.

One problem of the prior art porous tube diluters is the difficulty to adjust the dilution ratio with a high precision. Also controlling the temperature of the diluted flow is difficult with a prior art porous tube dilutor.

In FIG. 3 another prior art solution for diluting a sample is presented. The diluter type presented in FIG. 3 is called an ejector. In an ejector type configuration the dilution flow 22 is ejected into sample flow 21 typically in a quite a limited point of space. Sample flow 21 and dilution flow 22 mix and produce a diluted flow 23, which is then directed to an analyser 14. Problems of the prior art type ejectors relate to fouling and losses.

SUMMARY OF THE INVENTION

It is an object of this invention to overcome the disadvantages of the prior art. With an embodiment according to this invention the dilution process is easier to control and have fewer losses than the prior art solutions.

In an embodiment of the invention a sample flow is first diluted with a porous tube type dilution configuration and after that with an ejector type dilution configuration.

In another embodiment the transition delay between said two dilution configurations is so short that uncontrolled transformation of the sample are minimized.

In further embodiment the porous tube type dilution configuration includes two flow guides, one for dilution medium and another for cooling medium. These flow guides are separated by a wall comprising heat exchange means. These heat exchange means could comprise serrate shaped structures strengthening the heat exchange effect.

In the following a present invention will be described in more detail with the reference to the appended figures, in which

DECRIPTION OF THE PREFERRED EMBODIMENTS

Figure 1:
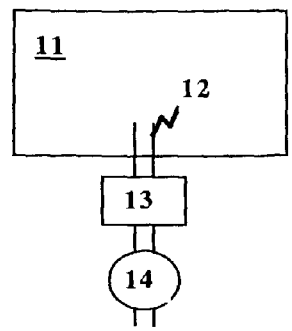
FIG 1 illustrates a prior art sampling method.
Figure 2:
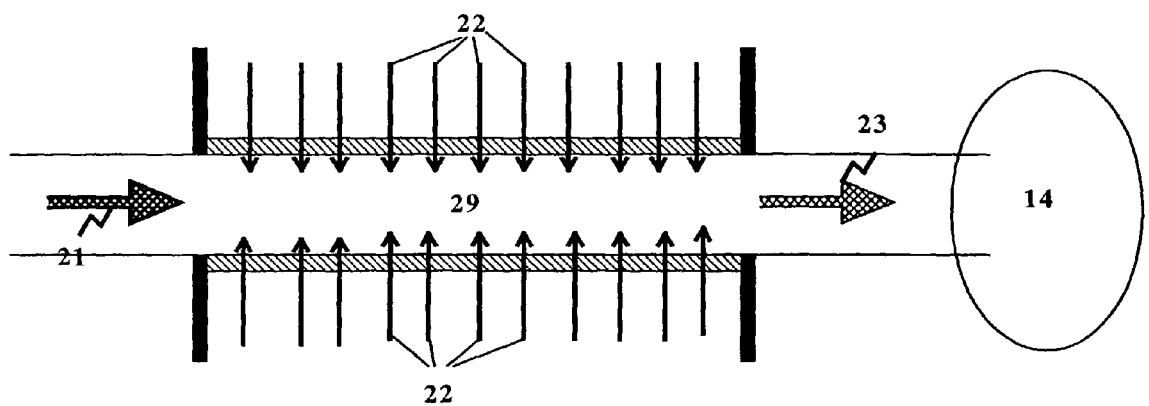
FIG 2 illustrates a prior art porous tube diluter.
Figure 3:
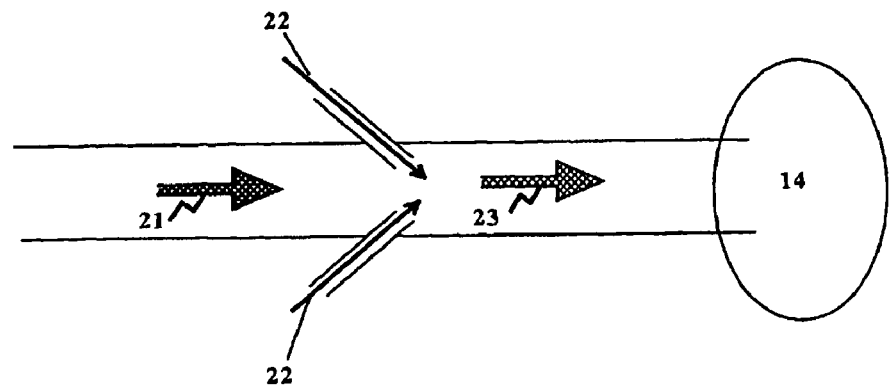
FIG 3 illustrates a prior art ejector type diluter.

FIGS. 1,2 and 3 have been described in relation to prior art.

In this text a term diluter is used, but that is not to be intended as limiting the scope of protection only to the devices called as diluters. It is e.g. possible to manufacture a single device comprising both the sample pre-processing and analysing and call that device an analyser, but still fall under the scope of this application. Thus the actual term used to call the device is not significant. What matters is the device including the parts identified in the accomplishing claims or their equivalents.

Figure 4:
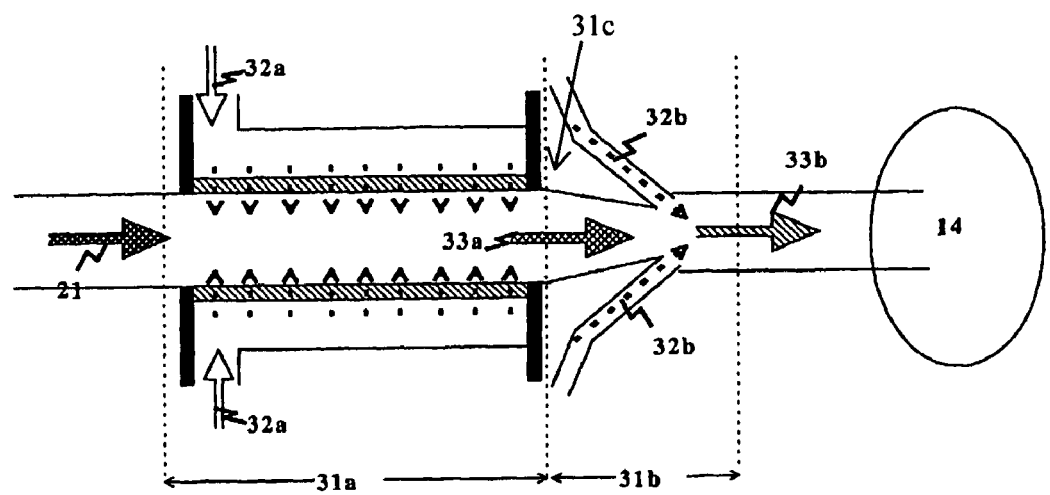
FIG 4 illustrates schematically an embodiment of the invention.

In FIG. 4 cross section of an embodiment of the invention is presented. The embodiment carries out the dilution in two phases, first the sample flow 21 is diluted by a first dilution flow 32a in a construction 31a similar to a porous tube diluter. This produces a first diluted flow 33a. First diluted flow 33a is then further diluted by a second dilution flow 32b directed to a said the first diluted flow 33a by a construction 31b similar to an ejector. The resulting second diluted flow 33b is directed to an analyser 14.

Carrying out the dilution in two phases gives clear benefits over the prior art solutions. Losses would be low because the first dilution flow 32a coming through the walls of the central cavity, would keep the sample flow away from the walls. In the ejector type configuration, which is more prone to losses, the first diluted flow 33a would already have a low density of the sample to be studied due the dilution done in the porous tube type configuration. Thus if the dilution in the first phase would be e.g. 1:10, then the losses produced by the ejector would by only 1/10th of the losses compared to an ejector used as a single device according to prior art solution.

The low losses are, however, achieved without sacrificing accuracy of controlling of the dilution ratio and temperature as would be the case if a prior art type solution based on a porous tube diluter would be used. As the second dilution is carried out by an ejector type configuration these parameters are easily controlled.

In one embodiment said two dilution phases are carried out so close to each other that there is no time for significant changes to characteristics like temperature of chemical composition the sample flow to happen. That is to say that the transition delay between two dilution phases is short compared to the uncontrolled transformations happening in the sample. One way of achieving this would be to place the porous tube type configuration and ejector type configuration so close to each other that the means 31c connecting them could be short compared to the velocity of the flow.

The means carrying out the first and second dilution can be arranged so that the exit opening of the porous tube type construction would be an entry opening for an ejector type construction. The two constructions could be built e.g. into a single case forming one combined device.

As the first and second dilution flows have slightly different objectives, in one embodiment of the invention the first dilution flow 32a and second dilution flow have separate control means. The two flows could even have separate sources of dilution medium, so that different mediums and temperatures could be used in the first and second dilution phases.

Figure 5:
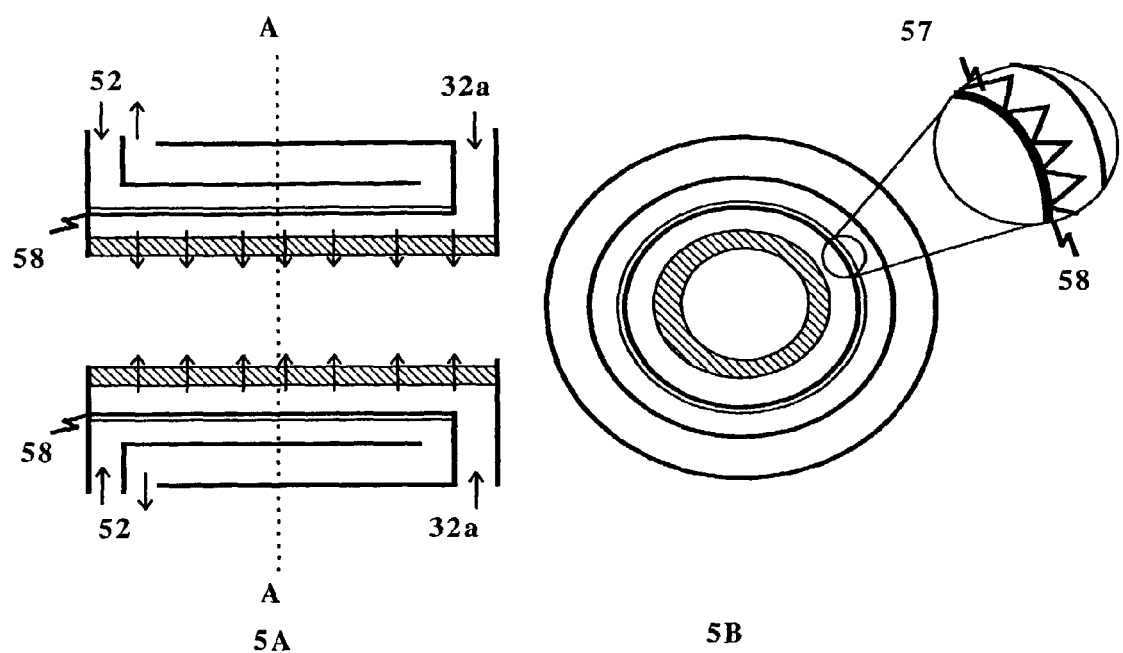
FIG 5 illustrates schematically another embodiment of the invention.

In FIGS. 5a and 5b two cross sections of a porous tube used in one embodiment of the invention are shown. FIG. 5b presents the cross section of the porous tube construction along the line A-A in FIG. 5a. The embodiment includes first flow guide or other similar means for delivering the first dilution flow 32a to the wall of porous tube known as such to a man skilled in the art. The temperature of the first dilution flow 32a as well as the temperature of the whole porous tube construction is controlled by a temperature control medium 52 i.e. cooling or heating agent, flowing in a second flow guide around the first flow guide.

To improve heat exchange between the first and second flow guides, one or both sides of the wall 58 separating the two flow guides can be equipped with a geometry improving heat exchange, like a serrate shaped structure 57. In the magnification in FIG 5 only the side of the second flow guide is equipped with a cooling serrature 57, but as stated above similar or different geometry could be applied also to the other side of the wall.

It is to be understood that although the present invention has been specially disclosed with preferred embodiments and examples, modifications to these may be apparent to a man skilled in the art and such modifications and variations are considered to be within the scope of the invention and the appended claims. It is also intended that all the matter contained in the above description shall be interpreted as illustrative and not in a limiting sense.

What is claimed is:

1. A device for diluting a sample, comprising:
a porous tube diluter,
an ejector diluter arranged downstream of the porous tube diluter, and
means for directing at least part of said sample from said porous tube diluter to said ejector diluter.

2. The device according to claim 1, wherein said means for directing are short compared to velocity of the flow so that the transport delay is so short that uncontrolled transformation of the sample are minimized.

3. The device according to claim 1, wherein said porous tube diluter comprises a first flow guide for directing a first dilution flow and means for controlling the temperature of a dilution medium flowing in said first flow guide.

4. The device according to claim 3, wherein said first flow guide and said means for controlling temperature are separated by a wall, said wall comprising heat exchange means.

5. The device according to claim 4, wherein said heat exchange means comprise cooling serrature.

6. The device according to claim 4, wherein said heat exchange means are located on the side of said temperature control means of said wall.

7. A method for diluting samples, comprising:
diluting a sample with a porous tube diluter,
directing at least part of the diluted sample to an ejector diluter, and
further diluting said at least part of the diluted sample with said ejector diluter.

8. The method according to claim 7, further comprising:
directing said at least part of the diluted sample to said ejector diluter before uncontrolled transformations of the sample substantially effect the composition of the diluted sample.

9. The method according to claim 7, further comprising:
controlling a temperature of a dilution medium flowing in said porous tube diluter with a cooling medium separated from said dilution medium by a wall comprising cooling serrature.

* * * * *

UNITED STATES PATENT AND TRADEMARK OFFICE
CERTIFICATE OF CORRECTION

Page 1 of 1

PATENT NO. : 7,759,131 B2
APPLICATION NO. : 10/173580
DATED : July 20, 2010
INVENTOR(S) : Mikkanen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2432 days.

Signed and Sealed this
Twenty-second Day of March, 2011

David J. Kappos
*Director of the United States Patent and Trademark Office*